(12) United States Patent
Cheung et al.

(10) Patent No.: US 11,611,223 B2
(45) Date of Patent: Mar. 21, 2023

(54) CHARGING ADAPTER FOR VAPORIZER DEVICE

(71) Applicant: JUUL Labs, Inc., San Francisco, CA (US)

(72) Inventors: Brandon Cheung, San Francisco, CA (US); Kevin Lomeli, San Francisco, CA (US); James Monsees, San Francisco, CA (US); Claire O'Malley, San Francisco, CA (US)

(73) Assignee: JUUL Labs, Inc., San Francisco, CA (US)

( * ) Notice: Subject to any disclaimer, the term of this patent is extended or adjusted under 35 U.S.C. 154(b) by 434 days.

(21) Appl. No.: 16/657,925

(22) Filed: Oct. 18, 2019

(65) Prior Publication Data

US 2020/0127475 A1    Apr. 23, 2020

Related U.S. Application Data

(60) Provisional application No. 62/748,150, filed on Oct. 19, 2018.

(51) Int. Cl.
*A24F 13/00* (2006.01)
*A24F 17/00* (2006.01)
(Continued)

(52) U.S. Cl.
CPC ......... *H02J 7/0042* (2013.01); *A61M 11/042* (2014.02); *A61M 2205/8206* (2013.01); *A61M 2205/8237* (2013.01)

(58) Field of Classification Search
CPC ....... A24F 40/10; A24F 40/90; A61M 11/042; A61M 2205/8206; A61M 2205/8237;
(Continued)

(56) References Cited

U.S. PATENT DOCUMENTS

| | | |
|---|---|---|
| 3,792,704 A | 2/1974 | Parker |
| 5,934,289 A | 8/1999 | Watkins et al. |

(Continued)

FOREIGN PATENT DOCUMENTS

| | | |
|---|---|---|
| CA | 2882464 C | 7/2017 |
| CA | 2920973 C | 9/2018 |

(Continued)

OTHER PUBLICATIONS (Jan. 6, 2018) User Manual Fitbit Blaze: "Table of Contents", Retrieved from the Internet: URL: https://staticcs.fitbit.com/content/assets/help/manuals/manual_blaze_en_US.pdf, 49 pages.

(Continued)

*Primary Examiner* — Abdullah A Riyami
*Assistant Examiner* — Thang H Nguyen
(74) *Attorney, Agent, or Firm* — Mintz Levin Cohn Ferris Glovsky and Popeo, P.C.

(57) ABSTRACT

A charging adapter assembly for charging a vaporizer device is described herein. In some embodiments, the charging adapter may include a housing including a coupling end configured to couple to the vaporizer device. The coupling end of the housing may include a chamber having a base and at least one chamber wall defining a perimeter of the chamber. The base may include at least one charging contact. The charging adapter may include a power adapter extending from the housing. The power adapter may be configured to provide an electrical pathway between a power source and the at least one charging contact. Related systems, methods, and articles of manufacture are also described.

20 Claims, 8 Drawing Sheets

(51) Int. Cl.
  *A24F 25/00* (2006.01)
  *H02J 7/00* (2006.01)
  *A61M 11/04* (2006.01)

(58) Field of Classification Search
  CPC ....... A61M 2205/8262; A61M 2209/04; H02J 7/0042
  See application file for complete search history.

(56) References Cited

U.S. PATENT DOCUMENTS

| | | | |
|---|---|---|---|
| 6,234,167 | B1 | 5/2001 | Cox et al. |
| 6,516,796 | B1 | 2/2003 | Cox et al. |
| 7,311,526 | B2 | 12/2007 | Rohrbach et al. |
| 7,500,479 | B2 | 3/2009 | Nichols et al. |
| D601,500 | S | 10/2009 | Green et al. |
| D611,409 | S | 3/2010 | Green et al. |
| 8,113,855 | B2 | 2/2012 | Green et al. |
| D697,029 | S | 1/2014 | Chiu |
| 8,899,238 | B2 | 12/2014 | Robinson et al. |
| 8,973,587 | B2 | 3/2015 | Liu |
| 8,978,663 | B2 | 3/2015 | Newton |
| 9,066,543 | B2 | 6/2015 | Cameron |
| D734,259 | S | 7/2015 | Cepress et al. |
| 9,089,166 | B1 | 7/2015 | Scatterday |
| 9,427,023 | B2 | 8/2016 | Liu |
| 9,615,791 | B2 * | 4/2017 | Zhang ............... H04B 5/02 |
| 9,641,208 | B2 | 5/2017 | Sela et al. |
| D790,463 | S | 6/2017 | Lai |
| D790,465 | S | 6/2017 | Zhao |
| 9,675,114 | B2 | 6/2017 | Timmermans |
| 9,795,168 | B2 | 10/2017 | Zhu |
| 10,069,320 | B2 | 9/2018 | Cai et al. |
| 10,420,708 | B2 | 9/2019 | Arric et al. |
| 10,439,419 | B2 | 10/2019 | Bernauer et al. |
| 10,575,562 | B2 | 3/2020 | Bless et al. |
| 10,834,969 | B2 | 11/2020 | Godfrey et al. |
| 10,834,973 | B2 | 11/2020 | Bless et al. |
| 11,123,504 | B2 * | 9/2021 | Alarcon ............... G02B 6/0051 |
| 2005/0225292 | A1 | 10/2005 | Damlamian et al. |
| 2007/0045276 | A1 | 3/2007 | Fisher et al. |
| 2007/0072443 | A1 | 3/2007 | Rohrbach et al. |
| 2007/0229025 | A1 | 10/2007 | Tsai et al. |
| 2008/0207276 | A1 | 8/2008 | Burrell |
| 2009/0283103 | A1 * | 11/2009 | Nielsen ............... A24F 40/60 131/273 |
| 2012/0060853 | A1 | 3/2012 | Robinson et al. |
| 2012/0223673 | A1 | 9/2012 | Chen et al. |
| 2012/0227753 | A1 | 9/2012 | Newton |
| 2013/0099725 | A1 | 4/2013 | Burrell et al. |
| 2014/0041655 | A1 | 2/2014 | Barron et al. |
| 2014/0053857 | A1 * | 2/2014 | Liu ............... A24F 40/90 131/329 |
| 2014/0060552 | A1 * | 3/2014 | Cohen ............... A61M 15/06 131/273 |
| 2014/0123989 | A1 | 5/2014 | Lamothe |
| 2014/0123990 | A1 | 5/2014 | Timmermans |
| 2014/0253144 | A1 | 9/2014 | Novak et al. |
| 2015/0009027 | A1 | 1/2015 | Harvey |
| 2015/0020831 | A1 * | 1/2015 | Weigensberg ......... A24F 40/50 131/329 |
| 2015/0141093 | A1 | 5/2015 | Sela et al. |
| 2015/0164142 | A1 | 6/2015 | Li et al. |
| 2015/0216235 | A1 | 8/2015 | Liu |
| 2015/0313284 | A1 | 11/2015 | Liu |
| 2015/0357839 | A1 | 12/2015 | Cai et al. |
| 2016/0021771 | A1 * | 1/2016 | Zhang ............... H04B 1/3888 361/752 |
| 2016/0106153 | A1 | 4/2016 | Zhu |
| 2016/0143358 | A1 | 5/2016 | Zhu |
| 2016/0219932 | A1 | 8/2016 | Glaser |
| 2016/0227837 | A1 | 8/2016 | Hammel et al. |
| 2016/0338405 | A1 | 11/2016 | Liu |
| 2016/0345625 | A1 | 12/2016 | Liu |
| 2016/0366935 | A1 | 12/2016 | Liu |
| 2017/0055579 | A1 | 3/2017 | Kuna et al. |
| 2017/0127726 | A1 | 5/2017 | Xiang |
| 2017/0135402 | A1 | 5/2017 | Zitzke |
| 2017/0208862 | A1 | 7/2017 | Li et al. |
| 2017/0215479 | A1 | 8/2017 | Kies |
| 2017/0215485 | A1 | 8/2017 | Zitzke |
| 2017/0250552 | A1 | 8/2017 | Liu |
| 2017/0295848 | A1 | 10/2017 | Lamothe |
| 2017/0302089 | A1 | 10/2017 | Bernauer et al. |
| 2018/0027878 | A1 * | 2/2018 | Dendy ............... H01M 10/46 |
| 2018/0103685 | A1 | 4/2018 | Yener |
| 2018/0116285 | A1 | 5/2018 | Polloni et al. |
| 2018/0116286 | A1 | 5/2018 | Polloni et al. |
| 2018/0117268 | A1 | 5/2018 | Selby et al. |
| 2018/0271167 | A1 * | 9/2018 | Memari ............... A24F 40/48 |
| 2019/0387791 | A1 * | 12/2019 | Pierce ............... A24F 40/60 |
| 2020/0028372 | A1 * | 1/2020 | Mahana ............... A61M 15/06 |
| 2020/0112188 | A1 * | 4/2020 | Cheung ............... H02J 7/00 |
| 2021/0161214 | A1 | 6/2021 | Bilat |

FOREIGN PATENT DOCUMENTS

| | | | |
|---|---|---|---|
| CN | 202004499 U | 10/2011 | |
| CN | 203087525 U | 7/2013 | |
| CN | 203168035 U | 9/2013 | |
| DE | 202014011273 U1 | 12/2018 | |
| DE | 102017222528 B3 | 1/2019 | |
| DE | 202014011284 U1 | 1/2019 | |
| DE | 202015009689 U1 | 3/2019 | |
| DE | 202015009690 U1 | 3/2019 | |
| EP | 1471955 B1 | 3/2015 | |
| EP | 2800489 B1 | 12/2015 | |
| EP | 3031339 A1 | 6/2016 | |
| EP | 2800485 B1 | 7/2016 | |
| EP | 3085257 A1 | 10/2016 | |
| EP | 3195738 A2 | 7/2017 | |
| EP | 2790537 B1 | 4/2018 | |
| EP | 3195738 B1 | 9/2018 | |
| EP | 3292771 B1 | 11/2018 | |
| EP | 3315034 B1 | 12/2018 | |
| EP | 3170414 B1 | 2/2019 | |
| EP | 3213385 B1 | 2/2019 | |
| EP | 2959784 B1 | 4/2019 | |
| EP | 3294348 B1 | 4/2019 | |
| EP | 3085257 B1 | 6/2019 | |
| EP | 2964037 B1 | 6/2020 | |
| EP | 3009017 B1 | 7/2020 | |
| EP | 3155910 B1 | 7/2020 | |
| EP | 3175507 B1 | 9/2020 | |
| EP | 3195737 B1 | 9/2020 | |
| EP | 3308661 B1 | 10/2020 | |
| EP | 3199042 B1 | 12/2020 | |
| EP | 2903466 B1 | 2/2021 | |
| EP | 3609356 B1 | 6/2021 | |
| GB | 2593118 A * | 9/2021 | ............ A24F 47/00 |
| KR | 20090010954 A | 1/2009 | |
| KR | 20090008914 U | 9/2009 | |
| WO | WO-0021598 A1 | 4/2000 | |
| WO | WO-2005106350 A2 | 11/2005 | |
| WO | WO-2007078273 A1 | 7/2007 | |
| WO | WO-2012026963 A2 | 3/2012 | |
| WO | WO-2013093695 A1 | 6/2013 | |
| WO | WO-2014071329 A1 | 5/2014 | |
| WO | WO-2014138244 A1 | 9/2014 | |
| WO | WO-2015054862 A1 | 4/2015 | |
| WO | WO-2015109616 A1 | 7/2015 | |
| WO | WO-2015100361 A1 | 7/2015 | |
| WO | WO-2015184747 A1 | 12/2015 | |
| WO | WO-2016019573 A1 | 2/2016 | |
| WO | WO-2016058189 A1 | 4/2016 | |
| WO | WO-2016058992 A2 | 4/2016 | |
| WO | WO-2016166661 A1 | 10/2016 | |
| WO | WO-2016166670 A1 | 10/2016 | |
| WO | WO-2016169796 A1 | 10/2016 | |
| WO | WO-2016172802 A1 | 11/2016 | |
| WO | WO-2017034597 A1 | 3/2017 | |
| WO | WO-2017064323 A1 | 4/2017 | |

(56) References Cited

FOREIGN PATENT DOCUMENTS

| | | |
|---|---|---|
| WO | WO-2017084920 A2 | 5/2017 |
| WO | WO-2017085240 A1 | 5/2017 |
| WO | WO-2020076866 A1 | 4/2020 |

OTHER PUBLICATIONS

User Manual Fitbit Flex "User Manual", Retrieved from the Web: https://staticcs.fitbit.com/content/assets/help/manuals/manual_flex_en_US.pdf. Retrieved on Feb. 17, 2020 32 Pages.

* cited by examiner

CHARGING ADAPTER FOR VAPORIZER DEVICE

CROSS REFERENCE

The present application claims priority to U.S. Provisional Patent Application No. 62/748,150 entitled "Charging Adapter for Vaporizer Device" filed Oct. 19, 2018, which is hereby incorporated by reference in its entirety.

TECHNICAL FIELD

The subject matter described herein relates to relates to a charging adapter, including a charging adapter configured to charge a vaporizer device.

BACKGROUND

Vaporizer devices, which can also be referred to as vaporizers, electronic vaporizer devices or e-vaporizer devices, can be used for delivery of an aerosol (or "vapor") containing one or more active ingredients by inhalation of the aerosol by a user of the vaporizing device. For example, electronic nicotine delivery systems (ENDS) include a class of vaporizer devices that are battery powered and that may be used to simulate the experience of smoking, but without burning of tobacco or other substances.

In use of a vaporizer device, the user inhales an aerosol, commonly called vapor, which may be generated by a heating element that vaporizes (e.g., causing a liquid or solid to at least partially transition to the gas phase) a vaporizable material, which may be liquid, a solution, a solid, a wax, or any other form as may be compatible with use of a specific vaporizer device. The vaporizable material used with a vaporizer can be provided within a cartridge (e.g., a separable part of the vaporizer that contains the vaporizable material in a reservoir) that includes a mouthpiece (e.g., for inhalation by a user).

To receive the inhalable aerosol generated by a vaporizer device, a user may, in certain examples, activate the vaporizer device by taking a puff, by pressing a button, or by some other approach. A puff, as the term is generally used (and also used herein), refers to inhalation by the user in a manner that causes a volume of air to be drawn into the vaporizer device such that the inhalable aerosol is generated by a combination of vaporized vaporizable material with the air.

The term vaporizer device, as used herein consistent with the current subject matter, generally refers to portable, self-contained, devices that are convenient for personal use. Typically, such devices are controlled by one or more switches, buttons, touch sensitive devices, or other user input functionality or the like (which can be referred to generally as controls) on the vaporizer, although a number of devices that may wirelessly communicate with an external controller (e.g., a smartphone, a smart watch, other wearable electronic devices, etc.) have recently become available. Control, in this context, refers generally to an ability to influence one or more of a variety of operating parameters, which may include without limitation any of causing the heater to be turned on and/or off, adjusting a minimum and/or maximum temperature to which the heater is heated during operation, interactive features that a user might access on a device, and/or other operations.

SUMMARY

Aspects of the current subject matter relate inter alia to a charging adapter assembly for charging a vaporizer device.

Some embodiments of the charging adapter assembly may include a housing including a coupling end configured to couple to the vaporizer device. The coupling end of the housing may include a chamber having a base and at least one chamber wall defining a perimeter of the chamber. The base may include at least one charging contact and a power adapter extending from the housing. The power adapter may be configured to provide an electrical pathway between a power source and the at least one charging contact.

In some variations of either the aspects explicitly called out above or others consistent with the current disclosure, one or more of the following features and/or others described herein or their equivalents may optionally be included in any feasible combination.

In one aspect, a first chamber wall of the at least one chamber wall may include a window configured to allow light to pass therethrough. The window may be positioned along the first chamber wall such that it may align with an indicator light along the vaporizer device when the vaporizer device is coupled to the charging adapter assembly. In some embodiments, the window may include a window area having a window wall thickness that is less than a chamber wall thickness of a part of the first chamber wall. The part of the first chamber wall may surround the window area. In some embodiments, the window area may include a material having an opacity of approximately 85 percent to approximately 99 percent.

In some embodiments, the at least one chamber wall may be made out of a flexible material thereby allowing deformation of the chamber. The flexible material may include a silicon material. The housing may include a structural support that is made out of a first material that is stiffer compared to the flexible material. The structural support may extend along a first chamber wall thereby allowing the first chamber wall to have a greater stiffness compared to a second chamber wall. The structural support may extend along a third chamber wall thereby allowing the first chamber wall and the third chamber wall to have a greater stiffness compared to the second chamber wall and a fourth chamber wall.

In some embodiments, the housing may include a structural support having a cutout that aligns with an indicator light along the vaporizer device when the vaporizer device is coupled to the charging adapter assembly. In some embodiments, the at least one charging contact may be positioned along the base to align with and contact at least one vaporizer contact along a charging end of the vaporizer device to allow charging of the vaporizer device.

In an interrelated aspect, a method of coupling a vaporizer device to a charging adapter assembly for charging the vaporizer device may include receiving a charging end of the vaporizer device in a chamber of the charging adapter assembly. The charging adapter assembly may include a housing including a coupling end configured to couple to the vaporizer device. The coupling end of the housing may include the chamber. The chamber may include a base and at least one chamber wall defining a perimeter of the chamber. The base may include at least one charging contact. A power adapter may extend from the housing. The power adapter may be configured to provide an electrical pathway between a power source and the at least one charging contact.

In an interrelated aspect, the method may further include allowing light emitted from an indicator light along the vaporizer device to be observed through the window. The indicator light may provide an indication of a charging state of the vaporizer device.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
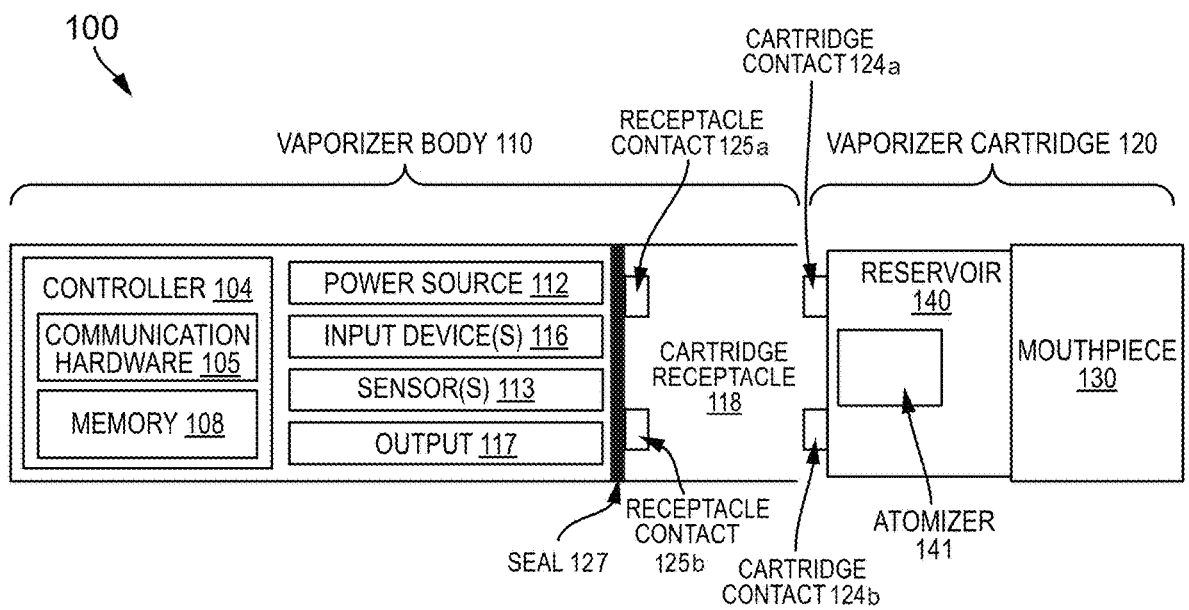
FIG. 1 illustrates a block diagram of a vaporizer consistent with implementations of the current subject matter.

Implementations of the current subject matter include methods, apparatuses, articles of manufacture, and systems relating to vaporization of one or more materials for inhalation by a user. Example implementations include vaporizer devices and systems including vaporizer devices. The term "vaporizer device" as used in the following description and claims refers to any of a self-contained apparatus, an apparatus that includes two or more separable parts (for example, a vaporizer body that includes a battery and other hardware, and a cartridge that includes a vaporizable material), and/or the like. A "vaporizer system," as used herein, can include one or more components, such as a vaporizer device. Examples of vaporizer devices consistent with implementations of the current subject matter include electronic vaporizers, electronic nicotine delivery systems (ENDS), and/or the like. In general, such vaporizer devices are hand-held devices that heat (such as by convection, conduction, radiation, and/or some combination thereof) a vaporizable material to provide an inhalable dose of the material.

The vaporizer device can include a power supply, such as a rechargeable battery. Certain rechargeable batteries may need to be recharged quickly so that the user can continue to use the vaporizer. Some vaporizers may be recharged by, for example, connecting the device to an external power supply via a wired connection or a USB connection with a desktop computer, and/or connected with a wall outlet. Some charging adapters can be used to couple a vaporizer to an external power supply to allow the vaporizer to recharge. Some vaporizer batteries may discharge after use and thus require recharging before subsequent use. The charging adapter assembly consistent with implementations of the current subject matter may provide an efficient and effective way to charge vaporizers, as will be described in greater detail below.

Typical portable charging devices may be heavy, difficult to carry, may be bulky, difficult to determine charging status of vaporizer (e.g., charging, charged, etc.), difficult to couple to a vaporizer for charging, and/or difficult to clean. The charging adapter assembly in accordance with implementations of the current subject matter can desirably provide a low profile charging adapter assembly that can secure and/or provide power to the vaporizer. The charging adapter assembly can be lightweight and/or less bulky compared to some currently available portable chargers. The charging adapter assembly can be generally aesthetically pleasing and/or easy to use. The charging adapter assembly can be easy to clean, which may prolong the effective and efficient functioning of the charger adapter assembly.

In some implementations, the charging adapter assembly may allow a charging indicator light to illuminate through at least a part of the charging adapter assembly thereby allowing a user to determine a charging status of the vaporizer, as will be described in greater detail below. In some embodiments, the charging adapter assembly may be flexible thereby allowing, for example, cleaning of internal areas of the charging adapter, and may include a structural support to provide structural integrity. Other benefits of the charging adapter assembly described herein can include providing efficient and effective coupling of a vaporizer to the charging adapter assembly. The charging adapter assembly can be made of one or more of a corrosion resistant material, a biocompatible material, plastic, aluminum, or other materials. Other features and benefits are within the scope of this disclosure.

A charging adapter assembly for a vaporizer device, consistent with features of one or more implementations of the current subject matter, may provide advantages and improvements relative to existing approaches, while also introducing additional benefits as described herein.

The vaporizable material used with a vaporizer device can be provided within a cartridge (for example, a part of the vaporizer that contains the vaporizable material in a reservoir or other container) which can be refillable when empty, or disposable such that a new cartridge containing additional vaporizable material of a same or different type can be used).

A vaporizer device can be a cartridge-using vaporizer device, a cartridge-less vaporizer device, or a multi-use vaporizer device capable of use with or without a cartridge. For example, a vaporizer device can include a heating chamber (for example, an oven or other region in which material is heated by a heating element) configured to receive a vaporizable material directly into the heating chamber, and/or a reservoir or the like for containing the vaporizable material. In some implementations, a vaporizer device can be configured for use with a liquid vaporizable material (for example, a carrier solution in which an active and/or inactive ingredient(s) are suspended or held in solution, or a liquid form of the vaporizable material itself), a paste, a wax, and/or a solid vaporizable material. A solid vaporizable material can include a plant material that emits some part of the plant material as the vaporizable material (for example, some part of the plant material remains as waste after the material is vaporized for inhalation by a user) or optionally can be a solid form of the vaporizable material itself, such that all of the solid material can eventually be vaporized for inhalation. A liquid vaporizable material can likewise be capable of being completely vaporized, or can include some portion of the liquid material that remains after all of the material suitable for inhalation has been vaporized.

Referring to the block diagram of FIG. 1, a vaporizer device 100 can include a power source 112 (for example, a battery, which can be a rechargeable battery), and a controller 104 (for example, a processor, circuitry, etc. capable of executing logic) for controlling delivery of heat to an atomizer 141 to cause a vaporizable material 102 to be converted from a condensed form (such as a solid, a liquid, a solution, a suspension, a part of an at least partially unprocessed plant material, etc.) to the gas phase. The controller 104 can be part of one or more printed circuit boards (PCBs) consistent with certain implementations of the current subject matter. After conversion of the vaporizable material 102 to the gas phase, at least some of the vaporizable material 102 in the gas phase can condense to form particulate matter in at least a partial local equilibrium with the gas phase as part of an aerosol, which can form some or all of an inhalable dose provided by the vaporizer device 100 during a user's puff or draw on the vaporizer device 100. It should be appreciated that the interplay between gas and condensed phases in an aerosol generated by a vaporizer device 100 can be complex and dynamic, due to factors such as ambient temperature, relative humidity, chemistry, flow conditions in airflow paths (both inside the vaporizer and in the airways of a human or other animal), and/or mixing of the vaporizable material 102 in the gas phase or in the aerosol phase with other air streams, which can affect one or more physical parameters of an aerosol. In some vaporizer devices, and particularly for vaporizer devices configured for delivery of volatile vaporizable materials, the inhalable dose can exist predominantly in the gas phase (for example, formation of condensed phase particles can be very limited).

The atomizer 141 in the vaporizer device 100 can be configured to vaporize a vaporizable material 102. The vaporizable material 102 can be a liquid. Examples of the vaporizable material 102 include neat liquids, suspensions, solutions, mixtures, and/or the like. The atomizer 141 can include a wicking element (i.e., a wick) configured to convey an amount of the vaporizable material 102 to a part of the atomizer 141 that includes a heating element (not shown in FIG. 1).

For example, the wicking element can be configured to draw the vaporizable material 102 from a reservoir 140 configured to contain the vaporizable material 102, such that the vaporizable material 102 can be vaporized by heat delivered from a heating element. The wicking element can also optionally allow air to enter the reservoir 140 and replace the volume of vaporizable material 102 removed. In some implementations of the current subject matter, capillary action can pull the vaporizable material 102 into the wick for vaporization by the heating element, and air can return to the reservoir 140 through the wick to at least partially equalize pressure in the reservoir 140. Other methods of allowing air back into the reservoir 140 to equalize pressure are also within the scope of the current subject matter.

As used herein, the terms "wick" or "wicking element" include any material capable of causing fluid motion via capillary pressure.

The heating element can include one or more of a conductive heater, a radiative heater, and/or a convective heater. One type of heating element is a resistive heating element, which can include a material (such as a metal or alloy, for example a nickel-chromium alloy, or a non-metallic resistor) configured to dissipate electrical power in the form of heat when electrical current is passed through one or more resistive segments of the heating element. In some implementations of the current subject matter, the atomizer 141 can include a heating element which includes a resistive coil or other heating element wrapped around, positioned within, integrated into a bulk shape of, pressed into thermal contact with, or otherwise arranged to deliver heat to a wicking element, to cause the vaporizable material 102 drawn from the reservoir 140 by the wicking element to be vaporized for subsequent inhalation by a user in a gas and/or a condensed (for example, aerosol particles or droplets) phase. Other wicking elements, heating elements, and/or atomizer assembly configurations are also possible.

Certain vaporizer devices may, additionally or alternatively, be configured to create an inhalable dose of the vaporizable material 102 in the gas phase and/or aerosol phase via heating of the vaporizable material 102. The vaporizable material 102 can be a solid-phase material (such as a wax or the like) or plant material (for example, tobacco leaves and/or parts of tobacco leaves). In such vaporizer devices, a resistive heating element can be part of, or otherwise incorporated into or in thermal contact with, the walls of an oven or other heating chamber into which the vaporizable material 102 is placed. Alternatively, a resistive heating element or elements can be used to heat air passing through or past the vaporizable material 102, to cause convective heating of the vaporizable material 102. In still other examples, a resistive heating element or elements can be disposed in intimate contact with plant material such that direct conductive heating of the plant material occurs from within a mass of the plant material, as opposed to only by conduction inward from walls of an oven.

The heating element can be activated in association with a user puffing (i.e., drawing, inhaling, etc.) on a mouthpiece 130 of the vaporizer device 100 to cause air to flow from an air inlet, along an airflow path that passes the atomizer 141 (i.e., wicking element and heating element). Optionally, air can flow from an air inlet through one or more condensation areas or chambers, to an air outlet in the mouthpiece 130. Incoming air moving along the airflow path moves over or through the atomizer 141, where vaporizable material 102 in the gas phase is entrained into the air. The heating element can be activated via the controller 104, which can optionally be a part of a vaporizer body 110 as discussed herein, causing current to pass from the power source 112 through a circuit including the resistive heating element, which is optionally part of a vaporizer cartridge 120 as discussed herein. As noted herein, the entrained vaporizable material 102 in the gas phase can condense as it passes through the remainder of the airflow path such that an inhalable dose of the vaporizable material 102 in an aerosol form can be delivered from the air outlet (for example, the mouthpiece 130) for inhalation by a user.

Activation of the heating element can be caused by automatic detection of a puff based on one or more signals generated by one or more of a sensor 113. The sensor 113 and the signals generated by the sensor 113 can include one or more of: a pressure sensor or sensors disposed to detect pressure along the airflow path relative to ambient pressure (or optionally to measure changes in absolute pressure), a motion sensor or sensors (for example, an accelerometer) of the vaporizer device 100, a flow sensor or sensors of the vaporizer device 100, a capacitive lip sensor of the vaporizer device 100, detection of interaction of a user with the vaporizer device 100 via one or more input devices 116 (for example, buttons or other tactile control devices of the vaporizer device 100), receipt of signals from a computing device in communication with the vaporizer device 100, and/or via other approaches for determining that a puff is occurring or imminent.

As discussed herein, the vaporizer device 100 consistent with implementations of the current subject matter can be configured to connect (such as, for example, wirelessly or via a wired connection) to a computing device (or optionally two or more devices) in communication with the vaporizer device 100. To this end, the controller 104 can include communication hardware 105. The controller 104 can also include a memory 108. The communication hardware 105 can include firmware and/or can be controlled by software for executing one or more cryptographic protocols for the communication.

A computing device can be a component of a vaporizer system that also includes the vaporizer device 100, and can include its own hardware for communication, which can establish a wireless communication channel with the communication hardware 105 of the vaporizer device 100. For example, a computing device used as part of a vaporizer system can include a general-purpose computing device (such as a smartphone, a tablet, a personal computer, some other portable device such as a smartwatch, or the like) that executes software to produce a user interface for enabling a user to interact with the vaporizer device 100. In other implementations of the current subject matter, such a device used as part of a vaporizer system can be a dedicated piece of hardware such as a remote control or other wireless or wired device having one or more physical or soft (i.e., configurable on a screen or other display device and selectable via user interaction with a touch-sensitive screen or some other input device like a mouse, pointer, trackball, cursor buttons, or the like) interface controls. The vaporizer device 100 can also include one or more outputs 117 or devices for providing information to the user. For example, the outputs 117 can include one or more light emitting diodes (LEDs) configured to provide feedback to a user based on a status and/or mode of operation of the vaporizer device 100.

In the example in which a computing device provides signals related to activation of the resistive heating element, or in other examples of coupling of a computing device with the vaporizer device 100 for implementation of various control or other functions, the computing device executes one or more computer instruction sets to provide a user interface and underlying data handling. In one example, detection by the computing device of user interaction with one or more user interface elements can cause the computing device to signal the vaporizer device 100 to activate the heating element to reach an operating temperature for creation of an inhalable dose of vapor/aerosol. Other functions of the vaporizer device 100 can be controlled by interaction of a user with a user interface on a computing device in communication with the vaporizer device 100.

The temperature of a resistive heating element of the vaporizer device 100 can depend on a number of factors, including an amount of electrical power delivered to the resistive heating element and/or a duty cycle at which the electrical power is delivered, conductive heat transfer to other parts of the electronic vaporizer device 100 and/or to the environment, latent heat losses due to vaporization of the vaporizable material 102 from the wicking element and/or the atomizer 141 as a whole, and convective heat losses due to airflow (i.e., air moving across the heating element or the atomizer 141 as a whole when a user inhales on the vaporizer device 100).

As noted herein, to reliably activate the heating element or heat the heating element to a desired temperature, the vaporizer device 100 may, in some implementations of the current subject matter, make use of signals from the sensor 113 (for example, a pressure sensor) to determine when a user is inhaling. The sensor 113 can be positioned in the airflow path and/or can be connected (for example, by a passageway or other path) to an airflow path containing an inlet for air to enter the vaporizer device 100 and an outlet via which the user inhales the resulting vapor and/or aerosol such that the sensor 113 experiences changes (for example, pressure changes) concurrently with air passing through the vaporizer device 100 from the air inlet to the air outlet. In some implementations of the current subject matter, the heating element can be activated in association with a user's puff, for example by automatic detection of the puff, or by the sensor 113 detecting a change (such as a pressure change) in the airflow path.

The sensor 113 can be positioned on or coupled to (i.e., electrically or electronically connected, either physically or via a wireless connection) the controller 104 (for example, a printed circuit board assembly or other type of circuit board). To take measurements accurately and maintain durability of the vaporizer device 100, it can be beneficial to provide a seal 127 resilient enough to separate an airflow path from other parts of the vaporizer device 100. The seal 127, which can be a gasket, can be configured to at least partially surround the sensor 113 such that connections of the sensor 113 to the internal circuitry of the vaporizer device 100 are separated from a part of the sensor 113 exposed to the airflow path. In an example of a cartridge-based vaporizer, the seal 127 can also separate parts of one or more electrical connections between the vaporizer body 110 and the vaporizer cartridge 120. Such arrangements of the seal 127 in the vaporizer device 100 can be helpful in mitigating against potentially disruptive impacts on vaporizer components resulting from interactions with environmental factors such as water in the vapor or liquid phases, other fluids such as the vaporizable material 102, etc., and/or to reduce the escape of air from the designated airflow path in the vaporizer device 100. Unwanted air, liquid or other fluid passing and/or contacting circuitry of the vaporizer device 100 can cause various unwanted effects, such as altered pressure readings, and/or can result in the buildup of unwanted material, such as moisture, excess vaporizable material 102, etc., in parts of the vaporizer device 100 where they can result in poor pressure signal, degradation of the sensor 113 or other components, and/or a shorter life of the vaporizer device 100. Leaks in the seal 127 can also result in a user inhaling air that has passed over parts of the vaporizer device 100 containing, or constructed of, materials that may not be desirable to be inhaled.

In some implementations, the vaporizer body 110 includes the controller 104, the power source 112 (for example, a battery), one more of the sensor 113, charging contacts (such as those for charging the power source 112), the seal 127, and a cartridge receptacle 118 configured to receive the vaporizer cartridge 120 for coupling with the vaporizer body 110 through one or more of a variety of attachment structures. In some examples, the vaporizer cartridge 120 includes the reservoir 140 for containing the vaporizable material 102, and the mouthpiece 130 has an aerosol outlet for delivering an inhalable dose to a user. The vaporizer cartridge 120 can include the atomizer 141 having a wicking element and a heating element. Alternatively, one or both of the wicking element and the heating element can be part of the vaporizer body 110. In implementations in which any part of the atomizer 141 (i.e., heating element and/or wicking element) is part of the vaporizer body 110, the vaporizer device 100 can be configured to supply the vaporizable material 102 from the reservoir 140 in the vaporizer cartridge 120 to the part(s) of the atomizer 141 included in the vaporizer body 110.

Cartridge-based configurations for the vaporizer device 100 that generate an inhalable dose of a vaporizable material 102 that is not a liquid, via heating of a non-liquid material, are also within the scope of the current subject matter. For example, the vaporizer cartridge 120 can include a mass of a plant material that is processed and formed to have direct contact with parts of one or more resistive heating elements, and the vaporizer cartridge 120 can be configured to be coupled mechanically and/or electrically to the vaporizer body 110 that includes the controller 104, the power source 112, and one or more receptacle contacts 125a and 125b configured to connect to one or more corresponding cartridge contacts 124a and 124b and complete a circuit with the one or more resistive heating elements.

In an embodiment of the vaporizer device 100 in which the power source 112 is part of the vaporizer body 110, and a heating element is disposed in the vaporizer cartridge 120 and configured to couple with the vaporizer body 110, the vaporizer device 100 can include electrical connection features (for example, means for completing a circuit) for completing a circuit that includes the controller 104 (for example, a printed circuit board, a microcontroller, or the like), the power source 112, and the heating element (for example, a heating element within the atomizer 141). These features can include one or more contacts (referred to herein as cartridge contacts 124a and 124b) on a bottom surface of the vaporizer cartridge 120 and at least two contacts (referred to herein as receptacle contacts 125a and 125b) disposed near a base of the cartridge receptacle 118 of the vaporizer device 100 such that the cartridge contacts 124a and 124b and the receptacle contacts 125a and 125b make electrical connections when the vaporizer cartridge 120 is inserted into and coupled with the cartridge receptacle 118. The circuit completed by these electrical connections can allow delivery of electrical current to a heating element and can further be used for additional functions, such as measuring a resistance of the heating element for use in determining and/or controlling a temperature of the heating element based on a thermal coefficient of resistivity of the heating element.

In some implementations of the current subject matter, the cartridge contacts 124a and 124b and the receptacle contacts 125a and 125b can be configured to electrically connect in either of at least two orientations. In other words, one or more circuits necessary for operation of the vaporizer device 100 can be completed by insertion of the vaporizer cartridge 120 into the cartridge receptacle 118 in a first rotational orientation (around an axis along which the vaporizer cartridge 120 is inserted into the cartridge receptacle 118 of the vaporizer body 110) such that the cartridge contact 124a is electrically connected to the receptacle contact 125a and the cartridge contact 124b is electrically connected to the receptacle contact 125b. Furthermore, the one or more circuits necessary for operation of the vaporizer device 100 can be completed by insertion of the vaporizer cartridge 120 in the cartridge receptacle 118 in a second rotational orientation such cartridge contact 124a is electrically connected to the receptacle contact 125b and cartridge contact 124b is electrically connected to the receptacle contact 125a.

In one example of an attachment structure for coupling the vaporizer cartridge 120 to the vaporizer body 110, the vaporizer body 110 includes one or more detents (for example, dimples, protrusions, etc.) protruding inwardly from an inner surface of the cartridge receptacle 118, additional material (such as metal, plastic, etc.) formed to include a portion protruding into the cartridge receptacle 118, and/or the like. One or more exterior surfaces of the vaporizer cartridge 120 can include corresponding recesses (not shown in FIG. 1) that can fit and/or otherwise snap over such detents or protruding portions when the vaporizer cartridge 120 is inserted into the cartridge receptacle 118 on the vaporizer body 110. When the vaporizer cartridge 120 and the vaporizer body 110 are coupled (e.g., by insertion of the vaporizer cartridge 120 into the cartridge receptacle 118 of the vaporizer body 110), the detents or protrusions of the vaporizer body 110 can fit within and/or otherwise be held within the recesses of the vaporizer cartridge 120, to hold the vaporizer cartridge 120 in place when assembled. Such an assembly can provide enough support to hold the vaporizer cartridge 120 in place to ensure good contact between the cartridge contacts 124a and 124b and the receptacle contacts 125a and 125b, while allowing release of the vaporizer cartridge 120 from the vaporizer body 110 when a user pulls with reasonable force on the vaporizer cartridge 120 to disengage the vaporizer cartridge 120 from the cartridge receptacle 118.

In some implementations, the vaporizer cartridge 120, or at least an insertable end of the vaporizer cartridge 120 configured for insertion in the cartridge receptacle 118, can have a non-circular cross section transverse to the axis along which the vaporizer cartridge 120 is inserted into the cartridge receptacle 118. For example, the non-circular cross section can be approximately rectangular, approximately elliptical (i.e., have an approximately oval shape), non-rectangular but with two sets of parallel or approximately parallel opposing sides (i.e., having a parallelogram-like shape), or other shapes having rotational symmetry of at least order two. In this context, approximate shape indicates that a basic likeness to the described shape is apparent, but that sides of the shape in question need not be completely linear and vertices need not be completely sharp. Rounding of both or either of the edges or the vertices of the cross-sectional shape is contemplated in the description of any non-circular cross section referred to herein.

The cartridge contacts 124a and 124b and the receptacle contacts 125a and 125b can take various forms. For example, one or both sets of contacts can include conductive pins, tabs, posts, receiving holes for pins or posts, or the like. Some types of contacts can include springs or other features to facilitate better physical and electrical contact between the contacts on the vaporizer cartridge 120 and the vaporizer body 110. The electrical contacts can optionally be gold-plated, and/or include other materials.

As discussed above, the vaporizer device may include a power supply, such as a rechargeable battery. Typical vaporizers may be rechargeable by, for example, connecting the vaporizer device to an external power supply via a wired connection or a USB connection with a desktop computer, and/or connected with a wall outlet. The charging adapter assembly consistent with implementations of the current subject matter may provide an efficient and effective way to charge vaporizers, as will be described in greater detail below.

The charging adapter assembly in accordance with implementations of the current subject matter may desirably provide a low profile charging adapter assembly that can secure and/or provide power to the vaporizer. The charging adapter assembly can be lightweight and/or less bulky compared to some currently available portable chargers. The charging adapter assembly can be generally aesthetically pleasing and/or easy to use. The charging adapter assembly can be easy to clean, which may prolong the effective and efficient functioning of the charging adapter assembly.

In some implementations, the charging adapter assembly may allow a charging indicator light of the vaporizer to illuminate through at least a part of the charging adapter assembly thereby allowing a user to determine a charging status of the vaporizer, as will be described in greater detail below. In some embodiments, the charging adapter assembly may be sufficiently flexible to achieve one or more benefits (e.g., allow cleaning of internal areas of the charging adapter) and may also include a structural support to provide structural integrity and other benefits (e.g., allow for efficient coupling of a vaporizer to the charging adapter assembly). The charging adapter assembly can be made out of one or more of a corrosion resistant material, biocompatible material, plastic, aluminum, and/or other materials. Other features and benefits are within the scope of this disclosure, some of which are described in further detail below.

Figure 2A:
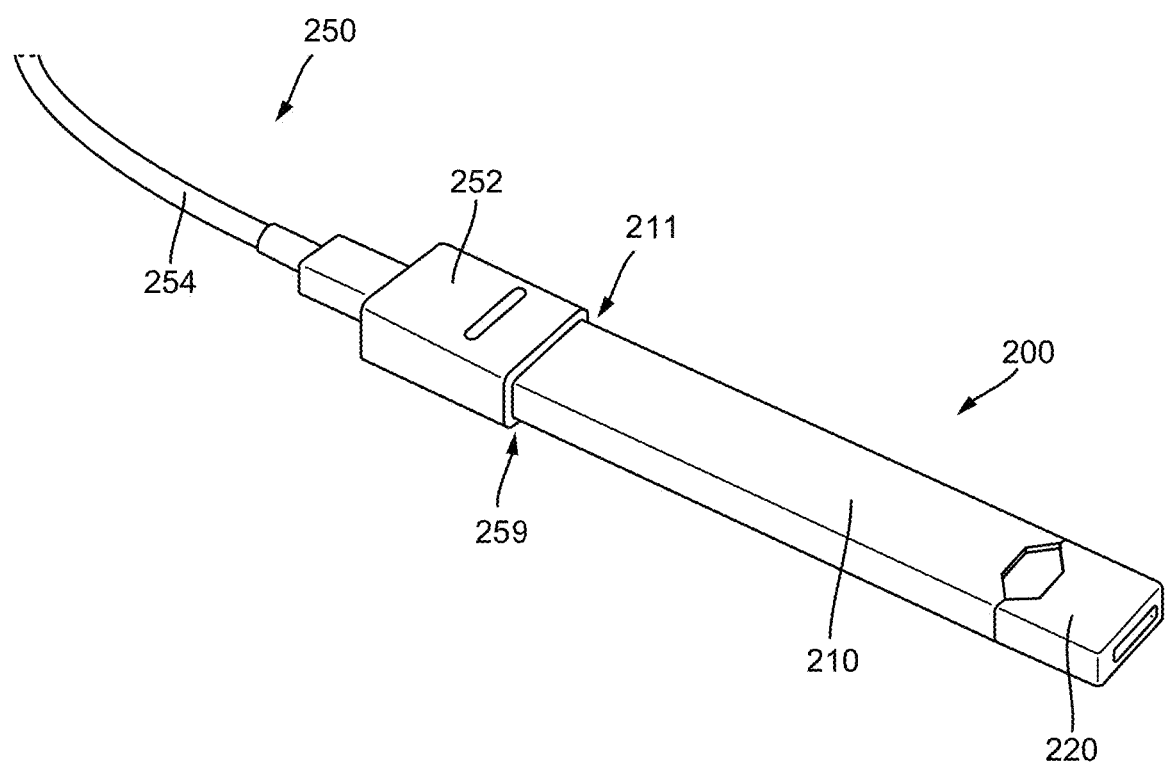
FIG. 2A illustrates a top perspective view of a vaporizer device coupled to an embodiment of a charging adapter assembly consistent with implementations of the current subject matter.

FIGS. 2A-2F illustrate an embodiment of a charging adapter assembly 250 consistent with implementations of the current subject matter. For example, FIG. 2A illustrates a vaporizer device 200 coupled to the charging adapter assembly 250. As shown in FIG. 2A, the charging adapter assembly 250 includes a charging body 252 with a cord 254 extending therefrom for connecting to an external power source (e.g., via a plug, USB feature, etc.). A charging end 211 of the vaporizer device 200, which may include one or more contacts (e.g., receptacle contacts 125a and 125b), may be inserted into a coupling end 259 of the charging body 252, thereby coupling the charging end 211 of the vaporizer device 200 to the charging body 252, as shown in FIG. 2A. Although shown as coupling the vaporizer body 210 of the vaporizer device 200 to the charging adapter assembly 250, some configurations of the charging adapter assembly 250 may be configured to accept a part of a cartridge 220 coupled to the vaporizer body 210.

Figure 2B:
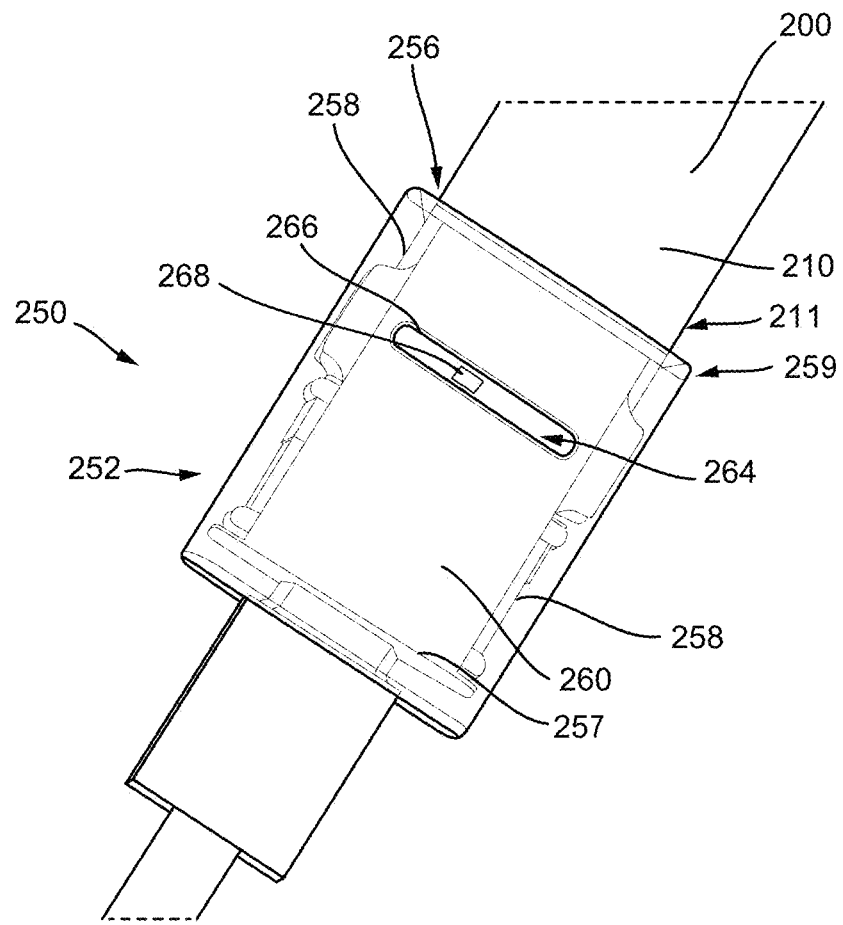
FIG. 2B illustrates a top transparent view of a distal end of the charging adapter assembly of FIG. 2A showing a charging body including a support.
Figure 2C:
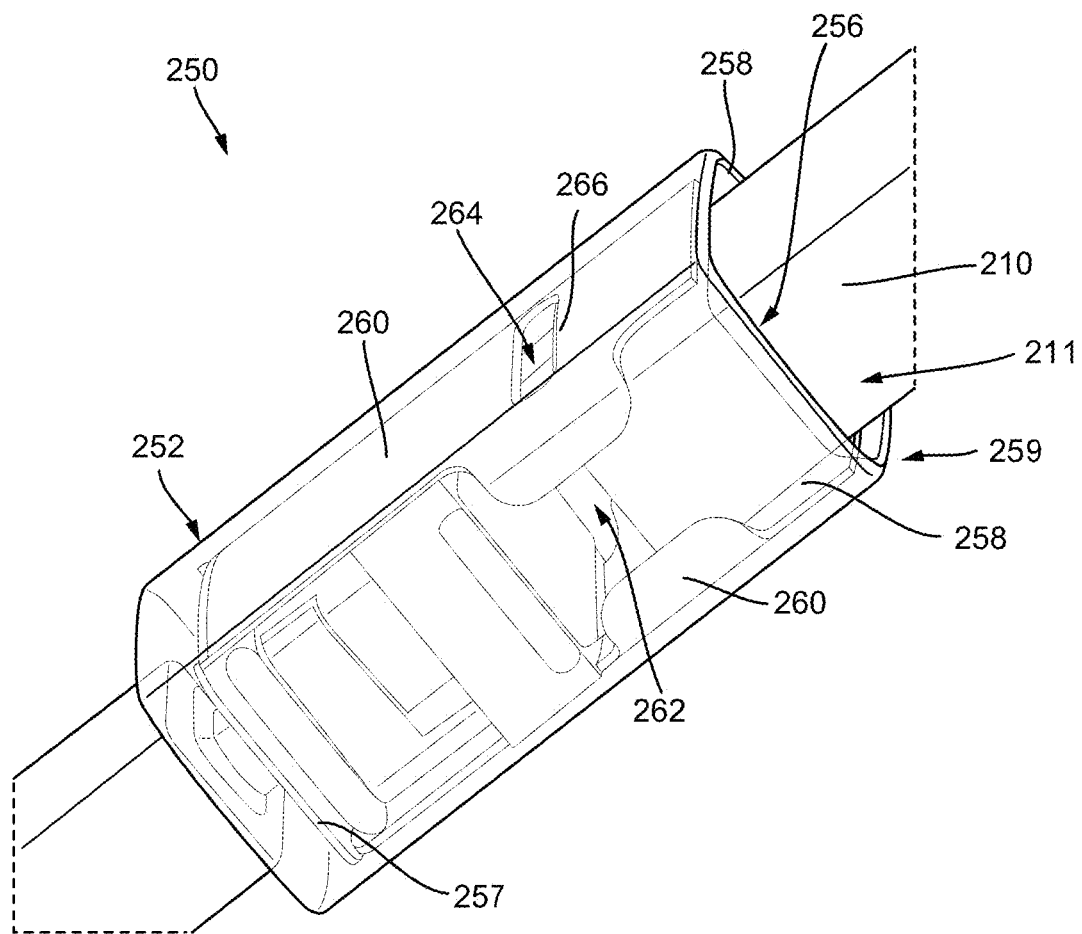
FIG. 2C illustrates a side perspective transparent view of the charging body of FIG. 2B showing the support.

As shown in FIGS. 2B and 2C, the charging body 252 may include a chamber 256 defined by a bottom surface 257 and chamber walls 258 forming a perimeter of the chamber 256. For example, the chamber 256 may include a square or rectangular volume defined by four chamber walls 258 extending between the bottom surface 257 of the chamber 256 and an end surface of the coupling end 259 of the charging body 252. As shown in FIGS. 2E and 2F, in some embodiments, the bottom surface 257 of the chamber 256 may include one or more charging contacts 261 that may mate with the one or more contacts of the vaporizer device 200 for charging the vaporizer device 200. The chamber walls 258 may provide coupling support between the vaporizer device 200 and charging body 252 and may assist in retaining the vaporizer device 200 in the chamber 256 of the charging body 252, such as during charging.

In some embodiments, the charging body 252 may be made out of a material that allows at least the chamber walls 258 to flex. For example, the chamber walls 258 may be made out of a material (e.g., silicon) that allows a user to insert a cleaning tool and/or finger into the chamber 256 thereby allowing the user to clean the chamber 256. Such cleaning of the chamber 256, which includes the charging contacts 261, may lengthen the lifespan and/or efficient and effective use of the charging adapter assembly 250 by allowing material that may interfere with charging to be removed from the chamber 256. Other benefits associated with such features may be appreciated and are within the scope of this disclosure.

Figure 2D:
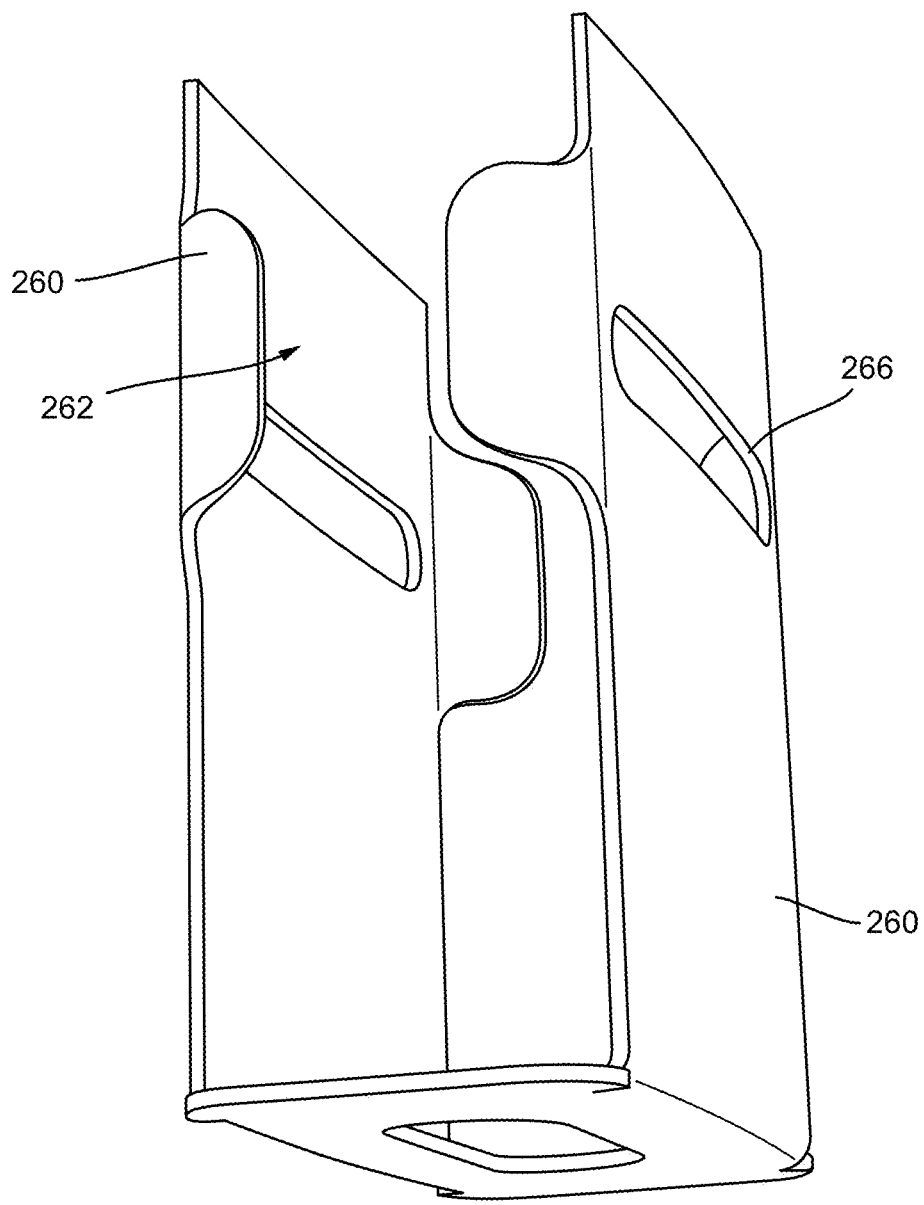
FIG. 2D illustrates a side perspective view of the support of FIG. 2C.
Figure 2E:
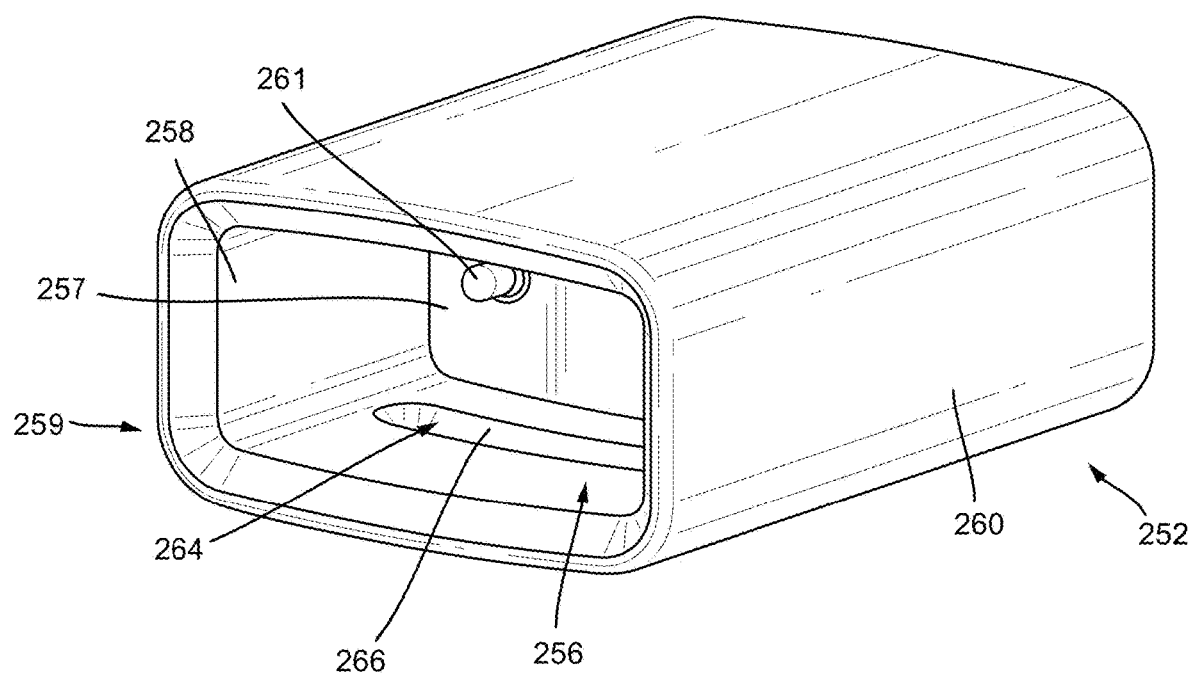
FIG. 2E illustrates a side isometric view of the charging body of FIG. 2B showing a window and a charging contact.
Figure 2F:
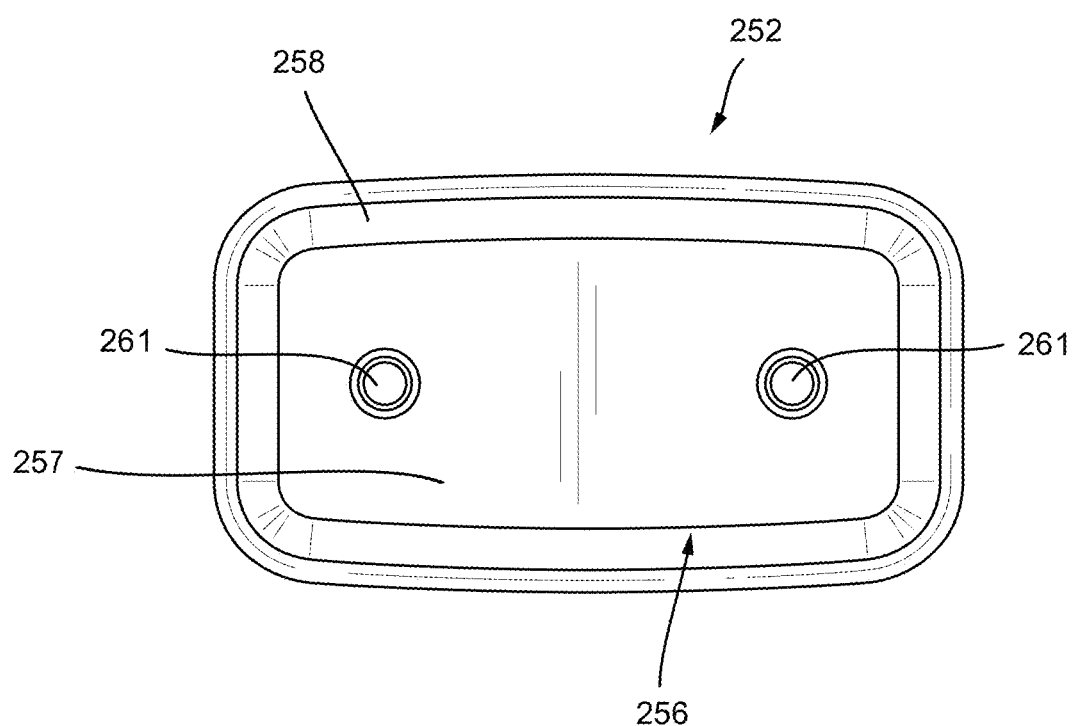
FIG. 2F illustrates an end view of the charging body of FIG. 2A showing a pair of charging contacts.

As shown in FIGS. 2B through 2D, the charging body 252 may include a support 260, which may be made out of a material that is stiffer compared to the charging body material. For example, the support 260 may be made out of a metal and molded into a part of the charging body 252 during manufacturing. In some implementations, the support 260 may substantially extend along two opposing walls of the charging body 252 and not extend along the remaining two opposing walls, as shown in FIG. 2C. Such configuration of the support 260 may limit the direction and extent the charging body 252 may flex. For example, as shown in FIGS. 2C and 2D, a gap 262 formed between opposing sides of the support 260 may allow the charging body 252 and/or chamber 256, including one or more of the chamber walls 258, to flex. For example, the ability of the chamber 256 to flex can allow opposing chamber walls 258 to be pushed towards and away from each other, which can assist with allowing the chamber 256 to be cleaned.

In some embodiments, some or all of the charging body 252 may be made out of a material having an opacity that allows a charging light 268 along the vaporizer device 200 to illuminate therethrough. For example, a substantial part of the charging body 252 may be made out of a material having an opacity of approximately 85% to approximately 99%, such as 95%. However, one or more parts of the charging body 252 may include a different material and/or structural property to allow light to travel therethrough.

As shown in FIG. 2B, the charging body 252 may include a window 264 configured to allow light emitted from the charging light 268 to pass through the window 264. In some embodiments, the window 264 may include a through hole that extends through the chamber wall 258. In some embodiments, the window 268 may include an area along the chamber wall 258 that includes a thinner wall thickness compared to a part of the chamber wall surrounding the window 264. Additionally or alternatively, in some embodiments the window 264 can include a different material property compared to a part of the chamber wall surrounding the window 264 (e.g., less than 50% opacity). For example, the window 264 may align with a charging light 268 on an embodiment of a vaporizer body 210 when the vaporizer body 210 is coupled to the charging body 252, as shown in FIG. 2B. As such, a user may be able to observe light emitted from the charging light 268 through the window 264 thereby allowing the user to determine the charging status of the vaporizer device 200, such as while the vaporizer device 200 is charging.

As shown in FIGS. 2B and 2D, the support 260 may include a cutout 266 that aligns with the window 264 thereby allowing the charging light 268 to illuminate through the charging body 252, including the support 260. For example, the cutout 266 may include a through-hole that is sized and shaped the same as or similar to the window 264. The cutout 266 can further provide support around the window 264 to ensure the charging light 268 is aligned with the window 264, thereby allowing light from the charging light 268 to pass through the cutout 266 and window 264.

Figure 3:
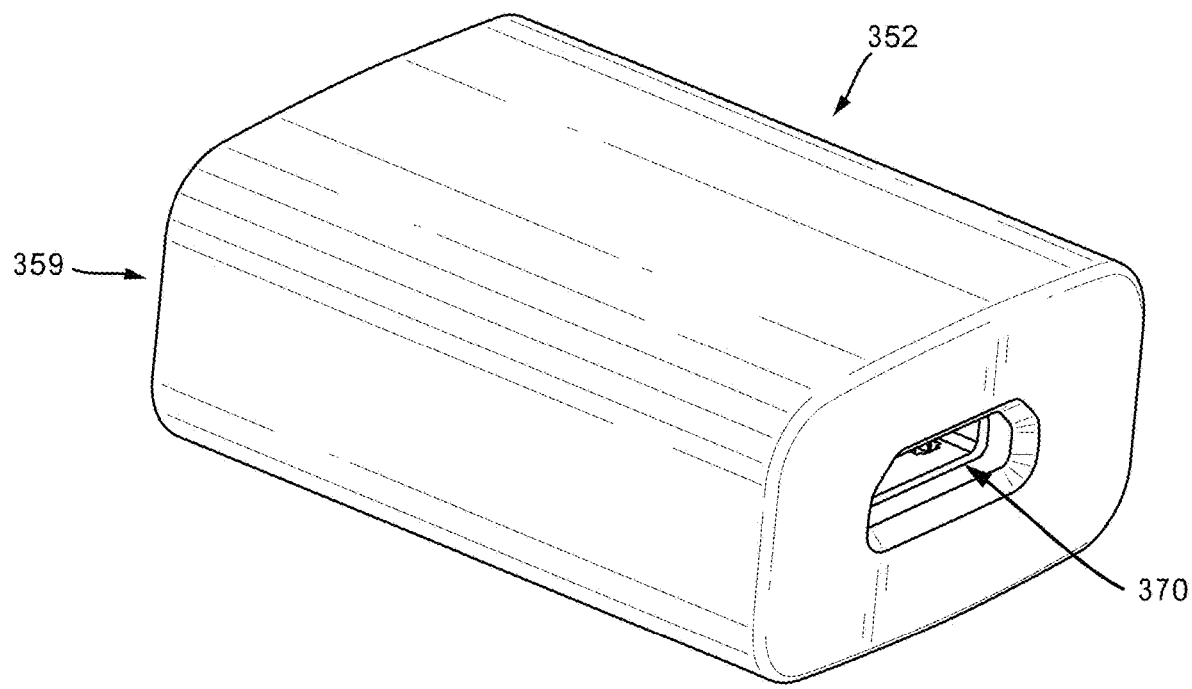
FIG. 3 illustrates a perspective view of another embodiment of a charging body including a charging port.

FIG. 3 illustrates an embodiment of the charging body 352 including a charging port 370. In some embodiments, the charging port 370 may be configured to couple to a power cord (e.g., cord 254), thereby providing electrical communication between an external power source and charging contacts of the charging body 352. The charging port 370 may be located on a side opposing the coupling end 359 of the charging body 352.

Terminology

When a feature or element is herein referred to as being "on" another feature or element, it can be directly on the other feature or element or intervening features and/or elements can also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements can be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature can have portions that overlap or underlie the adjacent feature.

Terminology used herein is for the purpose of describing particular embodiments and implementations only and is not intended to be limiting. For example, as used herein, the singular forms "a," "an," and "the" are intended to include the plural forms as well, unless the context clearly indicates otherwise.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device can be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers can be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value can have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes can be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Use of the term "based on," herein and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described herein can be directed to various combinations and subcombinations of the disclosed features and/or combinations and subcombinations of several further features disclosed herein. In addition, the logic flows depicted in the accompanying figures and/or described herein do not necessarily require the particular order shown, or sequential order, to achieve desirable results. Other implementations may be within the scope of the following claims.

What is claimed is:

1. A charging adapter assembly for charging a vaporizer device, comprising:
   a housing including a coupling end configured to couple to the vaporizer device, the coupling end of the housing including a chamber having a base and at least one chamber wall defining a perimeter of the chamber, the base including at least one charging contact, the at least one chamber wall formed out of a flexible material that allows deformation of the chamber, the housing including a structural support formed out of a first material that is stiffer compared to the flexible material, the structural support including a first support extension that extends along a first chamber wall thereby allowing the first chamber wall to have a greater stiffness compared to a second chamber wall; and
   a power adapter extending from the housing, the power adapter configured to provide an electrical pathway between a power source and the at least one charging contact.

2. The charging adapter assembly of claim 1, wherein the first chamber wall of the at least one chamber wall includes a window configured to allow light to pass therethrough.

3. The charging adapter assembly of claim 2, wherein the window is positioned along the first chamber wall such that it aligns with an indicator light along the vaporizer device when the vaporizer device is coupled to the charging adapter assembly.

4. The charging adapter assembly of claim 3, wherein the window includes a window area having a window wall thickness that is less than a chamber wall thickness of a part of the first chamber wall.

5. The charging adapter assembly of claim 4, wherein the part of the first chamber wall surrounds the window area.

6. The charging adapter assembly of claim 4, wherein the flexible material includes a material having an opacity of approximately 85 percent to approximately 99 percent.

7. The charging adapter assembly of claim 3, wherein the window includes a window area having a different material property than the first chamber wall.

8. The charging adapter assembly of claim 7, wherein the window area includes an opacity of less than 50 percent than the opacity of the first chamber wall.

9. The charging adapter assembly of claim 1, wherein the flexible material includes a silicon material.

10. The charging adapter assembly of claim 1, wherein the structural support includes a second support extension that extends along a third chamber wall thereby allowing the first chamber wall and the third chamber wall to have a greater stiffness compared to the second chamber wall and a fourth chamber wall.

11. The charging adapter assembly of claim 1, wherein the structural support includes a cutout that aligns with an indicator light along the vaporizer device when the vaporizer device is coupled to the charging adapter assembly.

12. The charging adapter assembly of claim 1, wherein the at least one charging contact is positioned along the base to align with and contact at least one vaporizer contact along a charging end of the vaporizer device to allow charging of the vaporizer device.

13. The charging adapter assembly of claim 1, wherein the first material of the structural support includes a metal material.

14. A method of coupling a vaporizer device to a charging adapter assembly for charging the vaporizer device, comprising:
receiving a charging end of the vaporizer device in a chamber of the charging adapter assembly, the charging adapter assembly, comprising:
a housing including a coupling end configured to couple to the vaporizer device, the coupling end of the housing including the chamber, the chamber including a base and at least one chamber wall defining a perimeter of the chamber, the base including at least one charging contact, the at least one chamber wall formed out of a flexible material that allows deformation of the chamber, the housing including a structural support formed out of a first material that is stiffer compared to the flexible material, the structural support including a first support extension that extends along a first chamber wall thereby allowing the first chamber wall to have a greater stiffness compared to a second chamber wall; and
a power adapter extending from the housing, the power adapter configured to provide an electrical pathway between a power source and the at least one charging contact.

15. The method of claim 14, wherein the first chamber wall of the at least one chamber wall includes a window configured to allow light to pass therethrough.

16. The method of claim 15, wherein the window is positioned along the first chamber wall such that it aligns with an indicator light along the vaporizer device when the vaporizer device is coupled to the charging adapter assembly.

17. The method of claim 16, wherein the window includes a window area having a different material property than the first chamber wall.

18. The method of claim 17, wherein the window area includes an opacity of less than 50 percent than the opacity of the first chamber wall.

19. The method of claim 14, wherein the structural support includes a second support extension that extends along a third chamber wall thereby allowing the first chamber wall and the third chamber wall to have a greater stiffness compared to the second chamber wall and a fourth chamber wall.

20. The method of claim 14, wherein the structural support includes a cutout that aligns with an indicator light along the vaporizer device when the vaporizer device is coupled to the charging adapter assembly.

* * * * *